United States Patent [19]

Kluger

[11] 4,427,597
[45] Jan. 24, 1984

[54] AMIDODICYANOALKANOLAMINES AND PROCESS FOR SELECTIVE CYANOALKYLATION OF AMIDODIALKANOLAMINES

[75] Inventor: Edward W. Kluger, Pauline, S.C.

[73] Assignee: Milliken Research Corporation, Spartanburg, S.C.

[21] Appl. No.: 346,788

[22] Filed: Feb. 8, 1982

[51] Int. Cl.$^3$ .......................................... C07C 121/417
[52] U.S. Cl. .................................. 260/465.4; 564/198
[58] Field of Search ...................... 260/465.4, 465.5 R, 260/465.6; 564/198

[56] References Cited

U.S. PATENT DOCUMENTS

| | | | |
|---|---|---|---|
| 2,326,721 | 8/1943 | Bruson | 260/465.5 R |
| 3,230,173 | 1/1966 | Spivack | 564/198 X |
| 3,560,551 | 2/1971 | Hillman | 260/465.4 |
| 4,001,304 | 1/1977 | Nyi et al. | 560/222 |

FOREIGN PATENT DOCUMENTS 505437  8/1954  Canada ................................ 564/198

OTHER PUBLICATIONS

"Cyanamid", The Chemistry of Acrylonitrile, 2nd Ed. (1959), p. 24.

*Primary Examiner*—Joseph Paul Brust
*Attorney, Agent, or Firm*—Terry T. Moyer; H. William Petry

[57] ABSTRACT

Nitrogen-containing compounds are provided of the formula:

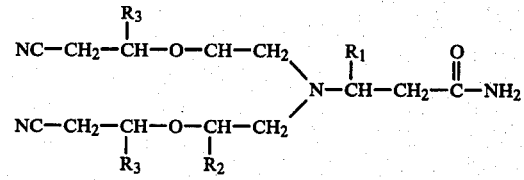

wherein $R_1$, $R_2$ and $R_3$ are each independently selected from H or a lower alkyl group having from 1 to about 6 carbon atoms. Also provided is a process involving selective cyanoalkylation of amidoalkyldialkanolamines whereby nitrogen-containing compounds may be prepared.

2 Claims, No Drawings

AMIDODICYANOALKANOLAMINES AND PROCESS FOR SELECTIVE CYANOALKYLATION OF AMIDODIALKANOLAMINES

The present invention relates to nitrogen-containing compounds and to a process whereby such nitrogen-containing compounds may be prepared.

Acrylonitrile and other chemically related ethylenically unsaturated nitriles have been widely available commercially at least since the end of World War II, and have become accepted as highly versatile chemical intermediates. Chemical reactions employing such compounds may involve the cyano (CN) group alone, the activated double bond (C=C), or even both groups.

While the most commercially important chemical reaction involving acrylonitrile is its polymerization, other known reactions include dimerization to prepare 1,2-dicyanocyclobutane, the Diels-Alder reaction with, for instance, butadiene to prepare Δ-3-tetrahydrobenzonitrile, hydrogenation to make propionitrile, among others.

Another known chemical reaction involving acrylonitrile and its chemically-related, ethylenically-unsaturated nitriles is the cyanoalkylation reaction (more commonly referred to where acrylonitrile is involved as cyanoethylation). The cyanoalkylation reaction involves the reaction of a suitable, ethylenically-unsaturated nitrile with active hydrogen compounds, thus introducing the cyanoalkyl group into the reacting molecule.

Active hydrogen compounds which have been reported as being suitable for use in this reaction include a variety of amines, amides, alcohols, mercaptans, aldehydes, ketones, esters, inorganic acids and their salts. American Cyanamid Company, Volume V, Cyanamid's Nitrogen Chemical Digest: the Chemistry of Acrylonitrile (1951 Beacon Press, N.Y., N.Y.) p. 26.

As to the cyanoalkylation of alcohols and other hydroxy compounds with acrylonitrile, the literature reports a large number of available, aliphatic, monohydric and polyhydric alcohols, as well as alcohols containing ether, tertiary amino and other non-reacting groups and phenols. See Table VI on pages 28–29 of the Cyanamid publication.

The list of amines which have been reported to be suitable for the cyanoalkylation reaction is also rather long, including aliphatic, aromatic and heterocyclic bases. See Table VIII, pages 32–33 of the Cyanamid publication.

The cyanoalkylation of some alkanolamines, the amines with which the present invention is, in general, concerned, has also been reported in the literature. (See J. A. Bell and C. Kenworthy, "Cyanoalkylation of Some Alkanolamines," *Communications Synthesis*, received July 12, 1971.) The Bell and Kenworthy publication also reports a one-step cyanoalkylation reaction between acrylonitrile and diethanolamine under relatively mild reaction conditions whereby a product containing predominant amounts (95 percent) of a corresponding N-substituted mono-cyanoethyl product compound is produced. While such compounds may be useful in their own right, they generally lack the high degree of nitrile functionality necessary in an intermediate compound which may be used to prepare an ultimate product, for instance, an amine having desired physical properties. At the same time such compounds of this general type offer the potential to be highly desirable for use in certain enduse applications due to certain physical properties inherent in the basic structure of the molecules. The process of the present invention provides a means by which the relatively high degree of functionality may be achieved in nitrogen-containing compounds made by the cyanoalkylation of amidoalkyldialkanolamines. The products resulting from such process are also considered to be within the scope of the present invention.

The nitrogen-containing compounds of the present invention may be represented by the following structural formula:

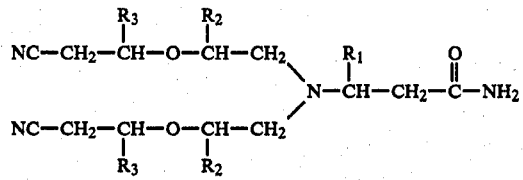

wherein $R_1$, $R_2$ and $R_3$ are each independently selected from H and a lower alkyl group having from 1 to about 6 carbon atoms. Preferably in the above structural formula $R_1$, $R_2$ and $R_3$ are all H.

The present invention also relates to a two-step process whereby the above-described, nitrile-containing compounds may be prepared. The process of the present invention comprises the steps of:

A. preferentially N-amidoalkylating at a temperature of from about 25° C. to about 60° C. a dialkanolamine of the formula:

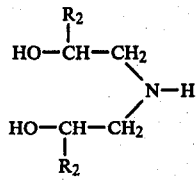

wherein $R_2$ is selected from H or a lower alkyl having from 1 to about 6 carbon atoms to provide an N-amidoalkyldialkanolamine with an ethylenically unsaturated amide of the formula

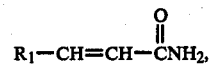

wherein $R_1$ is selected from H or a lower alkyl having from 1 to about 6 carbon atoms; and B. hydroxydicyanoalkylating said N-amidoalkyl-diakanolamine in the presence of an alkaline catalyst with an ethylenically unsaturated nitrile of the formula $R_3$—CH=CH—CN, wherein $R_3$ is selected from H or a lower alkyl group having from 1 to about 6 carbon atoms.

A preferred embodiment of the invention will be described with particular reference to acrylamide as the ethylenically unsaturated amide to be employed in Step A, the N-amidoalkylation step, and to acrylonitrile as the ethylenically unsaturated nitrile to be employed in Step B, the hydroxydicyanoalkylation step. It should be understood, however, that the invention is not to be limited to the use of acrylamide in Step A of the process. Another suitable ethylenically unsaturated amide which may be employed is, for instance, methacrylamide. It also should be understood that the invention is also not to be limited to the use of acrylonitrile in Step B of the process. Other suitable ethylenically unsaturated nitriles which may be employed include, for instance, crotonitrile and methacrylonitrile, to name just a few.

In accordance with a preferred embodiment, bis-2-cyanoethoxy-N-(propionamido)diethanolamine may be produced by the selective cyanoethylation of N-propionamidodiethanolamine with acrylonitrile either in the presence or absence of a solvent. First, preferential amidoethylation at the nitrogen position is accomplished with acrylamide. The intermediate N-amidoalkylated compound may then be further cyanoethylated in a second step at the hydroxy position with the aid of an alkaline catalyst. The corresponding amidodinitrile is produced in high yield as shown in the equation below:

to preferentially N-amidoethylate the desired dialkanolamine first prior to adding alkaline catalyst.

The temperature at which the hydroxydicyanoethylation occurs may vary widely. Generally, however, the temperature may be within a range of from about 30°–100° C. and preferably in the range of 30°–70° C. Likewise, the period of time required for the reaction to go to substantial completion may vary widely, such being dependent on the acrylonitrile concentration, alkaline catalyst concentration, solvent, as well as the temperature with which such reaction is carried out. Generally, however, the reaction proceeds to completion when the reactants are contacted at the required temperature for a period of time of from about 1–10 hours.

The hydroxydicyanoethylation may be accomplished in the presence of an alkaline catalyst. Typical of such cyanoethylation catalysts are sodium, potassium and

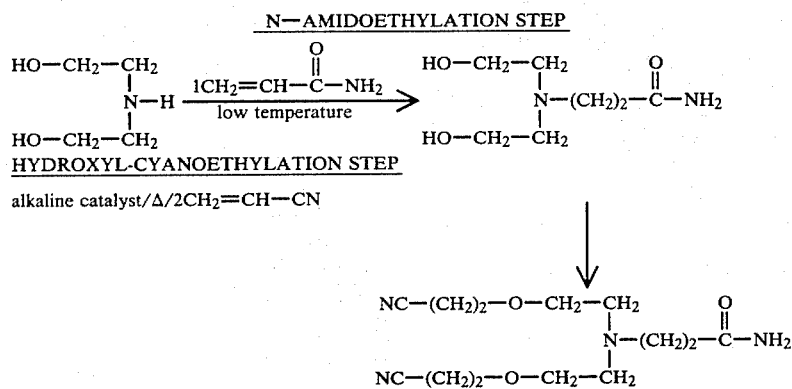

The temperature at which the preferential N-amidoethylation occurs is surprisingly low for a dialkylated amine. Dialkylated amines generally require long heating periods with excess acrylamide depending on the type of alkyl substituent. As a disadvantage of said prolonged heat temperature, discoloration and polymer formation may occur. Contrary to this undesired result, according to the present invention, dialkanol amines may be preferentially N-amidoethylated at a much lower temperature, thus avoiding the above-mentioned problems. Generally the temperature of the N-amidoethylation will vary within a range of from about 25°–80° C. and preferably in the range of 40°–60° C. Likewise, the period of time required for the reaction to go to substantial completion may vary widely, such being dependent on the acrylamide concentration as well as the temperature at which such reaction is carried out. Generally, however, the reaction proceeds to completion when the reactants are contacted at the required temperature for a period of time from about 10 minutes to about 5 hours.

The preferential N-amidoethylation may be carried out in the presence or absence of a solvent. When solvent is employed, any suitable solvent which will not interfere with the desired N-amidoethylation can be employed such as cycloaliphatic ethers, e.g., dioxane, tetrahydrofuran, and the like, and higher boiling hydrocarbons, e.g., hexane, cyclohexane, heptane, decane, toluene, xylenes, and the like, and alcohols, e.g., methyl alcohol, ethyl alcohol, isopropyl alcohol, isobutyl alcohol and the like. If alcohols are used in the preferential N-amidoethylation step, they must be removed prior to the hydroxydicyanoethylation step. It may be necessary lithium hydroxides. The amount of catalyst employed in the hydroxydicyanoethylation can vary widely. However, the amount of catalyst will vary from about 0.025 to 1 weight percent.

The hydroxydicyanoethylation may be carried out in the presence or absence of a solvent. When solvent is employed, any suitable solvent which will not interfere with the desired N-cyanoethylation can can be employed, such as cycloaliphatic ethers, e.g., dioxane, tetrahydrofuran and the like, and higher boiling hydrocarbons, e.g., hexane, cyclohexane, heptane, decane, toluene, xylenes and the like.

The nitrogen-containing compounds of the present invention may have a wide variety of end use applications that will be readily apparent to those skilled in the art. One particularly significant use, however, for the nitrogen containing compounds of the invention is as an intermediate compound which may be further processed by, for instance, hydrogenation of the cyanoalkyl group to the corresponding amidodiamines. These amidodiamines may be particularly useful as epoxy curing agents. One such hydrogenation step is described in a co-pending, commonly assigned patent application U.S. Ser. No. 346,720 filed Feb. 8, 1982, now U.S. Pat. No. 4,383,103, issued 5-10-83, entitled Aminoalkoxyamides and Epoxy Resin Compositions Containing Same having the same inventive entity as the present application. The disclosure of that application is incorporated herein by reference.

In order to more fully describe the subject matter of the present invention the following examples are given. Such examples, however, are presented for illustration only and are not to be construed as unduly limiting the scope of the present invention. Unless otherwise indicated, all parts and/or percentages given in these examples are by weight.

EXAMPLE 1

In a 500 cc three necked flask equipped with an overhead stirrer, reflux condenser, nitrogen purge, dropping funnel and thermometer, was charged 140.5 gms (0.8 moles) of diethanolamine (premelted). The overhead stirrer was then adjusted to high speed and the flask was preheated to ~40° C. with a water bath. Acrylamide was then added to the reaction flask. Over the course of 30 minutes, 56.7 gms (0.8 moles) of acrylamide was added, not allowing the reaction temperature to exceed 70° C. The reaction flask was then heated to 60°-70° C. (no further exotherm was observed) for an additional 2.5 hours. An IR spectrum showed the absence of any acrylamide and the presence of the corresponding N-propionamidodiethanolamine. A potentiometric titration of the amidoamine product with 1N HCl gave a neutralization equivalent of 5.67 milliequivalents of 1N HCl per 1 gm of product. The theoretical value of the amidoamine (MWT=176 g/mole) was calculated to be 5.68 milliequivalents of 1N HCl per gram of product, which is in good agreement with the observed experimental value. The amidoamine was used without further purification.

EXAMPLE 2

In a 2000 cc three necked flask equipped with an overhead stirrer, reflux condenser, nitrogen purge, dropping funnel and thermometer was charged 510.8 gms (2.9 moles) of N-propionamidodiethanolamine, and 0.5 gm of anhydrous lithium hydroxide. The overhead stirrer was then adjusted to high speed and the reaction contents were preheated to 40° C. with a water bath. Acrylonitrile was then added through the dropping funnel. Over the course of 1.5 hours a total of 422.7 cc (6.4 moles) of acrylonitrile was added and the reaction temperature reached a maximum of 80° C. with the water bath being maintained above 40° C. The reaction flask was then post heated at 55°-60° C. for an additional 3 hours. The reaction contents were cooled to room temperature and neutralized with acetic acid. The reaction contents were then filtered. The crude filtered reaction product was stripped of all excess acrylonitrile under vacuum (15-30 mmHg) and at a temperature not exceeding 70° C. to give the pale yellow liquid amidodinitrile. An IR spectrum showed the absence of acrylonitrile and the presence of the corresponding bis-(-2-cyanoethoxy)-N-propionamidodiethanolamine. The product was used without further purification.

EXAMPLE 3

In a 1000 cc three necked flask equipped with an overhead stirrer, reflux condenser, nitrogen purge, dropping funnel and thermometer, was charged 520 gms (3.90 moles) of diisopropanolamine (premelted). The overhead stirrer was then adjusted to high speed and the flask was preheated to ~40° C. with a water bath. Acrylamide was then added to the reaction flask. Over the course of 30 minutes, 277.2 gms (3.9 moles) of acrylamide was added, not allowing the reaction temperature to exceed 70° C. The reaction flask was then heated to 60°-70° C. (no further exotherm was observed) for an additional 2.5 hours. An IR spectrum showed the absence of any acrylamide and the presence of the corresponding N-propionamidodiisopropanol. This colorless viscous liquid was used without further purification.

EXAMPLE 4

In a 2000 cc three necked flask equipped with an overhead stirrer, reflux condenser, nitrogen purge, dropping funnel and thermometer was charged 345 gms (1.69 moles) of N-propionamidodiisopropanolamine and 1.0 gm of anhydrous lithium hydroxide. The overhead stirrer was then adjusted to high speed and the reaction contents were preheated to 40° C. with a water bath. Acrylonitrile was then added through the dropping funnel. Over the course of 1.5 hours a total of 246 cc (3.7 moles) of acrylonitrile was added and the reaction temperature reached a maximum of 80° C. with the water bath being maintained above 40° C. The reaction flask was then post heated at 55°-60° C. for an additional 3 hours. The reaction contents were cooled to room temperature and neutralized with acetic acid. The reaction contents were then filtered. The crude filtered reaction product was stripped of all excess acrylonitrile under vacuum (15-30 mmHg) and at a temperature not exceeding 70° C. to give the pale yellow liquid amidodinitrile. An IR spectrum showed the absence of acrylonitrile and the presence of the corresponding bis-(-2-cyanoethoxy)-N-propionamidodiisopropanolamine. The product was used without further purification.

What is claimed is:

1. Nitrile-containing compounds having the following formula:

$$\begin{array}{c}
R_3 \quad R_2 \\
| \quad | \\
NC-CH_2-CH-O-CH-CH_2 \\
\diagdown \\
N-CH-CH_2-C-NH_2 \\
\diagup \quad | \quad \| \\
NC-CH_2-CH-O-CH-CH_2 \quad R_1 \quad O \\
| \quad | \\
R_3 \quad R_2
\end{array}$$

wherein $R_1$, $R_2$ and $R_3$ are each independently selected from H or a lower alkyl group having from 1 to about 6 carbon atoms.

2. The nitrile-containing compounds of claim 1 wherein $R_1$, $R_2$ and $R_3$ are all H.

* * * * *